United States Patent
Bommarius et al.

(10) Patent No.: US 7,378,269 B2
(45) Date of Patent: May 27, 2008

(54) PROCESS FOR THE PRODUCTION OF AMINO ACIDS

(75) Inventors: Andreas Bommarius, Atlanta, GA (US); Karlheinz Drauz, Freigericht (DE); Stefan Verseck, Hanau (DE)

(73) Assignee: Degussa AG, Duesseldorf (DE)

( * ) Notice: Subject to any disclaimer, the term of this patent is extended or adjusted under 35 U.S.C. 154(b) by 965 days.

(21) Appl. No.: 10/651,965

(22) Filed: Sep. 2, 2003

(65) Prior Publication Data
US 2007/0148742 A1    Jun. 28, 2007

Related U.S. Application Data

(62) Division of application No. 09/973,765, filed on Oct. 11, 2001, now Pat. No. 6,656,710.

(30) Foreign Application Priority Data
Oct. 11, 2000 (DE) .............................. 100 50 123

(51) Int. Cl.
*C12P 41/00* (2006.01)
(52) U.S. Cl. ...................................... 435/280
(58) Field of Classification Search ................ None
See application file for complete search history.

(56) References Cited

U.S. PATENT DOCUMENTS

| 4,981,799 A | 1/1991 | Takahashi et al. |
| 5,858,759 A | 1/1999 | Neal et al. |
| 6,372,459 B1 | 4/2002 | Verseck et al. |
| 6,656,710 B2 * | 12/2003 | Bommarius et al. ........ 435/106 |

FOREIGN PATENT DOCUMENTS

| EP | 0 304 021 | 2/1989 |
| EP | 0 474 965 | 3/1992 |
| EP | 1 074 628 | 2/2001 |
| WO | 97/33987 | * 9/1997 |

OTHER PUBLICATIONS

Chen et al., "D-Aminoacylase from *Alcaligenes faecalis* Possesses Novel Activities on D-Methionine", Bioorganic & Medicinal Chemistry 2 (1) : 1-5 (1994).*
Sambale et al., "Studies on the enzymic hydrolysis of amino acid carbamates", Biotechnology and Applied Biochemistry 9 (3) : 251-7 (1987).*
Wakayama et al., "Cloning and sequencing of gene encoding D-aminoacylase from *Alcaligenes xylosoxydans* subsp. *xylosoxydans* A-6 and expression of the gene in *Escherichia coli*", Bioscience, Biotechnology and Biochemistry 59 (11) : 2115-19 (1995).*
U.S. Appl. No. 09/973,712, filed Oct. 11, 2001, Bommarius et al.
U.S. Appl. No. 10/651,965, filed Nov. 2, 2003, Bommarius et al.
U.S. Appl. No. 10/651,938, filed Nov. 2, 2003, Bommarius et al.

* cited by examiner

*Primary Examiner*—Sandra E. Saucier
(74) *Attorney, Agent, or Firm*—Oblon, Spivak, McClelland Maier & Neustadt, P.C.

(57) ABSTRACT

The present invention relates to the processes of racemization and deprotection of special N-protected amino acids in the acylase/racemase system for the total conversion of special N-protected racemic amino acids into optically pure amino acids.

6 Claims, No Drawings

PROCESS FOR THE PRODUCTION OF AMINO ACIDS

CROSS-REFERENCE TO RELATED APPLICATIONS

The present application claims priority to German Application DE 10050123.0, filed Oct. 11, 2000. The entire contents of the application is incorporated herein by reference.

BACKGROUND OF THE INVENTION

1. Field of the Invention

The present invention relates to the processes of racemization and deprotection of special N-protected amino acids in the acylase/racemase system for the total conversion of special N-protected racemic amino acids into optically pure amino acids.

2. Discussion of Background

Optically pure enantiomers of both L- and D-amino acids are important starting compounds in chemical syntheses, as well as for parenteral nutrition. Many methods of producing oprtically pure amino acids are possible and known to a person skilled in the art. Suitable processes include relevant enzymatic processes since they take place catalytically and produce with very high enantiomer concentrations of amino acids.

A racemic mixture of amino acids is not optically pure and contains both L-amino acid and D-amino acid enantiomers. Both L-amino acid and D-amino acid enantiomers can be utilized through enzymatic catalysis of a racemic mixture of N-protected amino acids. For example, it is known that L-amino acids are prepared from a racemic mixture of N-acetylated amino acids by using amino acid acylases. However, it is thought that these acylases are specific only for the cleavage of N-acetyl-protected amino acids and amines/alcohols (EP99118844.2; A. S. Bommarius et al., Tetrahedron; Asymmetry, 1997, Vol. 8, 3197-3200). Further, various racemization processes have been developed to prepare L-amino acids from the remaining D-acetyl amino acid fraction of the racemic mixture. DE 19935268.2 discloses an acetylamino acid racemase in the acylase/acetylamino acid racemase system that can prepare optically pure L-methionine from a racemic mixture of N-acetylmethionine.

Less specific N-acetylamino acid racemases (AAR) have been described previously. These racemases can be found in the microorganisms *Streptomyces atratus* Y-53 (Tokuyama et al., Appl. Microbiol. Biotechnol. 1994, 40, 835-840) and *Amycolatopis* sp. TS-1-60 (Tokuyama et al., Appl. Microbiol. Biotechnol. 1995a, 42, 853-859). For example, the racemase of *Amycolatopis* sp. TS-1-60 can catalyze the racemization of N-carbamoylamino acids to L-amino acids, although with less than optimal activity.

Processes for complete conversion of amino acids other than acetyl-protected or carbamoyl-protected amino acids to optically enriched amino acids are not known. Further, racemases with the ability to convert amino acids other than acetyl-protected or carbamoyl-protected amino acids are not known. Therefore, there is a need for enzymatic processes that racemize N-protected amino acids in general, as well as those N-protected amino acids other than acetyl-protected or carbamoyl-protected amino acids. The N-protected amino acid products of such racemic converstions may then be converted into the optically enriched amino acid by a subsequent enzymatic cleavage of the protecting group(s).

SUMMARY OF THE INVENTION

One object of the present invention is to provide the α-radical of a natural or synthetic amino acid of the formula (I):

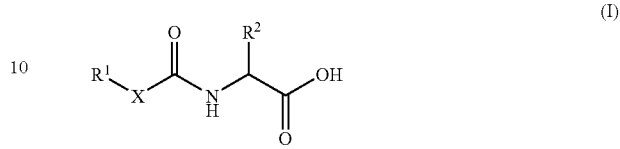

wherein
X=O, NH,
R=$CH_3$, $CH_3CH_2$, tert.-butyl, benzyl, wherein if X is NH then $R^1$ may be H, and $R^2$ denotes the α-radical of a natural or synthetic amino acid.

Another object of the present invention is a process for the racemization of N-protected amino acids, comprising contacting a compound of the general formula (I):

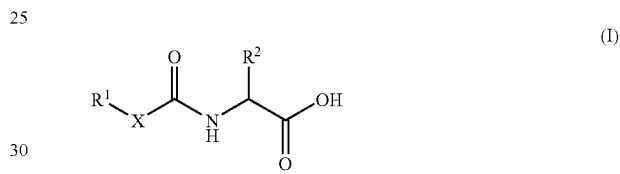

wherein
X=O, NH,
$R^1$=$CH_3$, $CH_3CH_2$, tert.-butyl, benzyl, wherein if X is NH, then $R^1$ may be H, and $R^2$ denotes the α-radical of a natural or synthetic amino acid, with an N-acetylamino acid racemase.

Another object of the present invention is a process for the cleavage of the protective group from N-protected amino acids, comprising contacting a compound of the general formula (I):

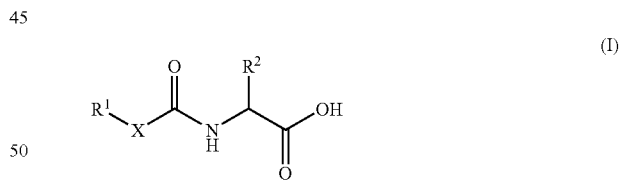

wherein
X=O, NH,
$R^1$=$CH_3$, $CH_3CH_2$, tert.-butyl, benzyl, wherein if X is NH, then $R^1$ may be H, and $R^2$ denotes the α-radical of a natural or synthetic amino acid, with an amino acid acylase.

Another object of the present invention is a process, comprising contacting an α-radical of a natural or synthetic amino acid of the formula (I) with an N-acetylamino acid racemase activity (AAR) in the presence of an amino acid acylase. In one embodiment, the racemase contacts the compound first followed by the acylase. Either or both the racemase and the acylase may be in a homogeneous free form, a recombinant free form, a part of a host organism, a portion of a digested cell mass, an immobilised form.

Another object of the present invention is to provide a process for the production of optically enriched amino acids from a racemic mixture of amino acids that are N-protected.

Another object of the present invention is to provide a process for the production of optically enriched amino acids from a racemic mixture of amino acids that are N-protected by means of a urethane-protected or carbamoyl-protected amino acid.

DETAILED DESCRIPTION OF THE INVENTION

Unless specifically defined, all technical and scientific terms used herein have the same meaning as commonly understood by a skilled artisan of molecular biology and biochemistry.

Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. Further, the materials, methods, and examples are illustrative only and are not intended to be limiting.

Reference is made to standard textbooks of molecular biology that contain definitions and methods and means for carrying out basic scientific techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and various references cited therein.

The term "α-radical of an amino acid" is understood to denote the radical located on the α-C atom of an α-amino acid. This radical may be derived from a natural amino acid, as described in Beyer-Walter, Lehrbuch der organischen Chemie, S. Hirzel Verlag Stuttgart, $22^{nd}$ Edition, 1991, p. 822f. Furthermore, corresponding α-radicals of synthetic α-amino acids are also covered, as listed for example in DE19903268.8.

"Optically enriched", or "enantiomer-enriched", compounds within the scope of the present invention is understood to mean the presence of an optical antipode mixed with the other antipodes in a concentration of >50 mole %.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins, which comprise two or more amino acids, bonded via peptide bonds.

"Free form" of a polynucleotide or polypeptide refers to a polynucleotide or polypeptide separated out of its natural environment and into an aqueous solution.

"Digested cell mass" is any solution of cellular components produced as a direct result of disrupting the integrity of a cell wall and/or cell membrane. The cell may be a unicellular organism and/or may be a portion of a multicellular organism.

"N-acetylamino acid racemase" denotes a class of enzymes that can racemise optically enriched N-acetylamino acids. On account of the great similarity to one another, all N-acetylamino acid racemases known to the person skilled in the art can be used for the present conversions. Preferably, the racemases to be used are those from *Streptomyces atratus* Y-53 as well as *Amycolatopis* sp. TS-1-60. A process that is particularly preferred is one comprising the N-acetylamino acid racemase from *Amycolatopsis orientalis* subspecies *lurida* (SEQ ID NO. 2), since this particular N-acetylamino acid racemase has advantages over other representatives of this class of compounds with regard to dependence on metal ions and activity (EP99118844.2) This enzyme is encoded by the polynucleotide of SEQ ID NO. 1.

Also included in the present invention are those racemases having amino acid sequences that are at least 70, 80, 85, 90, 95, and 98% identical to SEQ ID NO. 2 and which have racemase activity.

Homology, sequence similarity, or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments, i.e. aligning all of one sequence with all of another similar sequence, using the method of Needleman and Wunsch, J. Mol. Biol. 48:443-453 (1970). When using a sequence alignment program such as BestFit, to determine the degree of sequence homology, similarity, or identity, the default setting may be used, or an appropriate scoring matrix may be selected to optimize identity, similarity, or homology scores. Similarly, when using a program such as BestFit to determine sequence identity, similarity, or homology between two different amino acid sequences, the default settings may be used, or an appropriate scoring matrix, such as blosum45 or blosum80, may be selected to optimize identity, similarity, or homology scores.

Further racemases that may be used according to the invention are those portions or fragments of the above-mentioned polypeptides exhibiting any enzymatic racemization of optically enriched N-acetylamino acids.

Methods for determining racemase activity of polypeptides have been described previously. The analysis can thus be carried out, for example, by reacting enantiomer-pure amino acid derivatives in the presence of a solution containing at least one polypeptide and following the formation of a corresponding racemate using a polarimeter (Perkin-Elmer 241) at various wavelengths. The reaction can be carried out at temperatures ranging from 15 to 55° C. (heatable cell) for time increments from 3 to 12 hours in reaction media deemed appropriate for optimizing racemase activity. For example, the reaction media can be buffered at a pH ranging from 5.0 to 9.0 and can include divalent metal ion salt concentrations ranging from 1 to 15 mM.

"Amino acid acylases" within the scope of the invention is understood to denote enzymes that deacetylate N-acylamino acids in a stereospecific manner. In principle all representatives of this class of compound known to the person skilled in the art are suitable for the reactions according to the invention and may be employed. It is preferred, however, to employ amino acid acylases such as the L-specific acylase I or D-specific acylase from *Aspergillus oryzae*. Both amino acid acylases can be obtained from Amano International Enzyme Company at 1157 N Main Street, Lombard, Ill. 60148.

Further acylases that may be used for the reaction are described in the following literature citations: Wakayama M, Yada H, Kanda S, Hayashi S, Yatsuda Y, Sakai K, Moriguchi M, Role of conserved histidine residues in D-aminoacylase from *Alcaligenes xylosoxydans* subsp. *xylosoxydans* A-6, Biosci. Biotechnol. Biochem. 2000 January; 64(1):1-8; Wakayama M, Hayashi S, Yatsuda Y, Katsuno Y, Sakai K, Moriguchi M., Overproduction of D-aminoacylase from *Alcaligenes xylosoxydans* subsp. *xylosoxydans* A-6 in *Escherichia coli* and its purification, Protein Expr. Purif. 1996 June; 7(4):395-9; Wakayama M, Katsuno Y, Hayashi S, Miyamoto Y, Sakai K, Moriguchi M., Cloning and sequencing of a gene encoding D-aminoacylase from *Alcaligenes xylosoxydans* subsp. *xylosoxydans* A-6 and expression of the gene in *Escherichia coli*, Biosci. Biotechnol. Biochem. 1995 November; 59(11):2115-9; Wakayama M, Ashika T, Miyamoto Y, Yoshikawa T, Sonoda Y, Sakai K, Moriguchi M.; Primary structure of N-acyl-D-glutamate amidohydrolase from *Alcaligenes xylosoxydans* subsp. *xylosoxydans* A-6, J. Biochem. (Tokyo). 1995 July; 118(1): 204-9; Chen H P, Wu S H, Wang K T., D-Aminoacylase from *Alcaligenes faecalis* possesses activities on D-methionine, Bioorg. Med. Chem. 1994 January; 2(1):1-5; Moriguchi M, Sakai K, Miyamoto Y, Wakayama M., Production, purification, and characterization of D-aminoacylase from *Alcaligenes xylosoxydans* subsp. *xylosoxydans* A-6, Biosci. Biotechnol. Biochem. 1993 July; 57(7):1149-52; Yang Y B, Hsiao K M, Li H, Yano H, Tsugita A, Tsai Y C, Characterization of D-aminoacylase from *Alcaligenes denitrificans* DA181, Biosci. Biotechnol. Biochem. 1992 September; 56(9):1392-5; Tsai Y C, Lin C S, Tseng T H, Lee H, Wang Y J, Production and immobilization of D-aminoacylase of *Alcaligenes faecalis* DA1 for optical resolution of N-acyl-DL-amino acids, Enzyme Microb. Technol. 1992 May; 14(5):384-9; Batisse N, Weigel P, Lecocq M, Sakanyan V., Two amino acid amidohydrolase genes encoding L-stereospecific carbamoylase and aminoacylase are organized in a common operon in *Bacillus stearothermophilus*, Appl. Environ. Microbiol. 1997 February; 63(2):763-6; Yang Y B, Hu H L, Chang M C, Li H, Tsai Y C, Purification and characterization of L-aminoacylase from *Alcaligenes denitrificans* DA181, Biosci. Biotechnol. Biochem. 1994 January; 58(1):204-5; Jakob M, Miller Y E, Rohm K H, Cloning and sequence analyses of cDNAs encoding aminoacylase I from porcine kidney, Biol. Chem. Hoppe Seyler. 1992 December; 373(12):1227-31; Mitta M, Ohnogi H, Yamamoto A, Kato I, Sakiyama F, Tsunasawa S., The primary structure of porcine aminoacylase 1 deduced from cDNA sequence, J. Biochem. (Tokyo). 1992 December; 112(6): 737-42; Bommarius A S, Drauz K, Klenk H, Wandrey C., Operational stability of enzymes. Acylase-catalyzed resolution of N-acetyl amino acids to enantiomerically pure L-amino acids, Ann. N Y Acad. Sci. 1992 Nov. 30; 672: 126-36; Gentzen I, Loffler H G, Schneider F., Aminoacylase from *Aspergillus oryzae*. Comparison with the pig kidney enzyme, Z. Naturforsch. [C]. 1980 July-August; 35(7-8): 544-50.

Further acylases that may be used according to the invention are those portions of the above-mentioned polypeptides exhibiting any deacetylation of N-acylamino acids in a stereospecific manner.

Methods for determining acylase activity of polypeptides on various N-protected amino acids have been described previously. The analysis can thus be carried out, for example, by reacting various N-protected amino acids derivatives in the presence of a solution containing at least one polypeptide and following the increasing presence of the unmodified N-amino acid. The reaction can be carried out at temperatures ranging from 15 to 55° C. (heatable cell) for time increments from 3 to 12 hours in reaction media deemed appropriate for optimizing acylase activity. For example, the reaction media can be buffered at a pH ranging from 5.0 to 9.0 and can include divalent metal ion salt concentrations ranging from 1 to 15 mM.

The invention also provides host organisms which express one or both of the racemase and acylase described herein. These enzymes may be expressed from the chromosome, either as endogenous or inserted by recombinations, or from a vector or plasmid existing episomally. These organisms can be cultured continuously or discontinuously in the batch process (batch culture) or in the fed batch (feed process) or repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Digested cell mass may be produced, for example, from cell lysis methods described in Glenney, Jr., J. R. and Zokas, L. (1989). J. Cell Biol. 108:2401; Glenney, Jr., J. R. (1991). Meth. Enzymology 201:92; Maniatis et al., Molecular Cloning: A Laboratory Manual, Cold Spring Harbor Laboratory, New York (1982); Sambrook et al., Molecular Cloning: A Laboratory Manual, Cold Spring Harbor Laboratory, New York (1989) and various references cited therein. Such cell lysis methods may be performed on unicellular organisms or cells from multicellular organisms which may or may not express one or both of the racemase and acylase described herein.

N-acetylamino acid racemases and amino acid acylases may be used together, or successively, in the free form as homogeneously purified compounds or as enzymes produced by recombinant techniques. In addition the enzymes may also be used as a constituent of a host organism (whole cell catalyst as in US09/407062) or in combination with the digested cell mass of the host organism. It is also possible to use the enzymes in immobilised form (Bhavender P. Sharma, Lorraine F. Bailey and Ralph A. Messing, "Immobilisierte Biomaterialiem—Techniken und Anwendungen", Angew. Chem. 1982, 94, 836-852). The immobilisation is advantageously carried out by lyophilisation (Dordick et al. J. Am. Chem. Soc. 194, 116, 5009-5010; Okahata et al. Tetrahedron Lett. 1997, 38, 1971-1974; Adlercreutz et al. Biocatalysis 1992, 6, 291-305). The lyophilisation is preferably carried out in the presence of surfactants such as Aerosol OT, polyvinylpyrrolidone, polyethylene glycol (PEG), or Brij 52 (diethylene glycol monocetyl ether) (Goto et al. Biotechnol. Techniques 1997, 11, 375-378).

The reaction according to the invention is preferably carried out in an enzyme-membrane reactor (DE 199 10 691.6).

Methods for the determination of N-amino acids have been described previously. The analysis can thus be carried out, for example, as described in Spackman et al. (Analytical Chemistry, 30, (1958), 1190) by anion exchange chromatography with subsequent ninhydrin derivation, or it can be carried out by reversed phase HPLC, for example as described by Lindroth et al. (Analytical Chemistry (1979) 51: 1167-1174).

The present invention is explained in more detail with the aid of the following embodiment examples. The microorganism, *Amycolatopsis orientalis* subsp. *lurida*, has been filed at the German Collection for Microorganisms under Number DSM43134.

EXAMPLES

Example 1

Detection of the Racemase Activity of a Recombinant N-acetylamino acid Racemase AAR Enzyme The substrate spectrum of the N-acetylamino acid racemase (AAR) from *Amycolatopsis orientalis* subsp. *lurida* was tested with the enzyme assay described herein below.

The composition of the assay was as follows:

| | |
|---|---|
| Buffer Tris/HCl | 50 mM (pH 8.0) |
| Substrate | 25 mM |
| Cobalt chloride | 6 mM |
| AAR | ca. 150 µg purified protein |
| Final volume | 1 ml |

Enantiomer-pure amino acid derivatives were used in the assay and the formation of the corresponding racemate was followed using a polarimeter (Perkin-Elmer 241). The incubation was carried out at 30° C. (heatable cell) for 3 to 12 hours. The measurements were made at a wavelength of $\lambda$=365 nm.

TABLE 1

List of the tested substrates and corresponding specific activity of the AAR.

| Substrate | Specific Activity |
|---|---|
| N-methyloxycarbonyl-L-Met | 42 mU/mg |

Example 2

Producing D-Met and L-Met from Moc-L-Met

Moc-L-Met was used in an assay to determine the activity of the L-acylase from *Aspergillus oryzae*.

A. Producing L-Met from Moc-L-Met

| | |
|---|---|
| Buffer Tris/HCl | 50 mM (pH 8.0) |
| Moc-L-Met | 25 mM |
| Cobalt chloride | 6 mM |
| L-Acylase | 2.0 U |
| (*Aspergillus oryzae*) | |
| Final volume | 200 µL |
| Volume activity: | 1.4 U/ml |

B. Producing D-Met from Moc-L-Met

Moc-L-Met was used in an assay to determine the activity of the D-acylase from *Aspergillus oryzae* in the presence of an N-acetylamino acid racemase (AAR) from *Amycolatopsis orientalis* subsp. *lurida*.

| | |
|---|---|
| Buffer Tris/HCl | 50 mM (pH 8.0) |
| Moc-L-Met | 25 mM |
| Cobalt chloride | 6 mM |
| D-Acylase | 2.4 U |
| (Amano International Enzyme Company at 1157 N Main Street, Lombard, IL 60148) | |
| AAR | 0.4 U |
| Final volume | 200 µL |
| Volume activity: | 0.6 U/ml |

D-Met and L-Met were detected by reverse phase HPLC (RP18). The unit data for the enzymes refer to specific activity with N-Ac-L-Met and N-Ac-D-Met as substrate.

Numerous modifications and variations on the present invention are possible in light of the above teachings. It is, therefore, to be understood that within the scope of the accompanying claims, the invention may be practiced otherwise than as specifically described herein.

What is claimed is:

1. A method for producing an amino acid, comprising:

contacting a compound of formula (I) with an amino acid acylase wherein the L-amino acid acylase is L-specific amino acid acylase (I) from *Aspergillus oryzae*;

wherein formula (I) is:

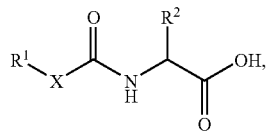

wherein

X=O, NH, $R^1$=$CH_3$, $CH_3 CH_2$, tert butyl, benzyl, wherein if X is NH then $R^1$ is H and P7 denotes the α-radical of a natural or synthetic amino acid; and recovering the amino acid produced.

2. The method according to claim 1, wherein the amino acid acylase is homogeneously purified.

3. The method according to claim 1, wherein the amino acid acylase is a recombinant amino acid acylase.

4. The method according to claim 1, wherein amino the acid acylase is a part of a host organism.

5. The method according to claim 1, wherein the amino acid acylase is a portion of a digested cell mass.

6. The method according to claim 1, wherein the amino acid acylase is immobilised.

* * * * *

SEQUENCE LISTING

```
<160> NUMBER OF SEQ ID NOS: 2

<210> SEQ ID NO 1
<211> LENGTH: 1107
<212> TYPE: DNA
<213> ORGANISM: Amycolatopsis orientalis
<220> FEATURE:
<221> NAME/KEY: CDS
<222> LOCATION: (1)..(1107)
<223> OTHER INFORMATION:

<400> SEQUENCE: 1 gtg aaa ctc agc ggt gtg gaa ctg cgc cgg gtc cgg atg ccg ctc gtg       48
Val Lys Leu Ser Gly Val Glu Leu Arg Arg Val Arg Met Pro Leu Val
1               5                   10                  15 gcc ccg ttc cgg acg tcg ttc ggg acg cag tcc gag cgg gaa ttg ctg       96
Ala Pro Phe Arg Thr Ser Phe Gly Thr Gln Ser Glu Arg Glu Leu Leu
            20                  25                  30
```

```
ctg gtc cgc gcg gtg acc ccg gcg ggc gag ggc tgg ggc gaa tgt gtc    144
Leu Val Arg Ala Val Thr Pro Ala Gly Glu Gly Trp Gly Glu Cys Val
         35                  40                  45 gcg atg gag gcg ccg ctc tac tcg tcg gag tac aac gac gcc gcc gag    192
Ala Met Glu Ala Pro Leu Tyr Ser Ser Glu Tyr Asn Asp Ala Ala Glu
 50                  55                  60 cac gtg ctg cgg aac cat ctg atc ccc gca ctg ctg gcg gcc gag gac    240
His Val Leu Arg Asn His Leu Ile Pro Ala Leu Leu Ala Ala Glu Asp
 65                  70                  75                  80 gtg acc gcg cac aag gtg acg ccg ttg ctg gcg aag ttc aag ggc cac    288
Val Thr Ala His Lys Val Thr Pro Leu Leu Ala Lys Phe Lys Gly His
                     85                  90                  95 cgg atg gcg aag ggc gcg ctg gag atg gcg gtc ctc gac gcc gaa ctc    336
Arg Met Ala Lys Gly Ala Leu Glu Met Ala Val Leu Asp Ala Glu Leu
            100                 105                 110 cgc gcg cat gac cgg tcc ttc gcg gcc gag ctg ggg tcc act cgc gac    384
Arg Ala His Asp Arg Ser Phe Ala Ala Glu Leu Gly Ser Thr Arg Asp
        115                 120                 125 tcc gtg gcc tgc ggg gtc tcg gtc ggg atc atg gac tcg atc ccg cac    432
Ser Val Ala Cys Gly Val Ser Val Gly Ile Met Asp Ser Ile Pro His
    130                 135                 140 ctg ctc gac gtc gtc ggc ggc tac ctc gac gag ggc tac gtc cgg atc    480
Leu Leu Asp Val Val Gly Gly Tyr Leu Asp Glu Gly Tyr Val Arg Ile
145                 150                 155                 160 aag ctg aag atc gag ccc ggc tgg gac gtc gag ccg gtc cgg cag gtg    528
Lys Leu Lys Ile Glu Pro Gly Trp Asp Val Glu Pro Val Arg Gln Val
                165                 170                 175 cgt gag cgc ttc ggt gac gac gtg ctg ctg cag gtc gac gcg aac acc    576
Arg Glu Arg Phe Gly Asp Asp Val Leu Leu Gln Val Asp Ala Asn Thr
            180                 185                 190 gcg tac acg ctg ggc gac gcg ccc ctg ctg tcc cgg ctc gac ccg ttc    624
Ala Tyr Thr Leu Gly Asp Ala Pro Leu Leu Ser Arg Leu Asp Pro Phe
        195                 200                 205 gac ctg ctg ctg atc gag cag ccg ctc gaa gaa gag gac gtg ctc ggc    672
Asp Leu Leu Leu Ile Glu Gln Pro Leu Glu Glu Glu Asp Val Leu Gly
    210                 215                 220 cac gcc gag ctg gcc aag cgg atc cgg acg ccg atc tgc ctc gac gag    720
His Ala Glu Leu Ala Lys Arg Ile Arg Thr Pro Ile Cys Leu Asp Glu
225                 230                 235                 240 tcg atc gtc tcg gcc aag gcc gcc gcg gac gcg atc aag ctc ggc gcc    768
Ser Ile Val Ser Ala Lys Ala Ala Ala Asp Ala Ile Lys Leu Gly Ala
                245                 250                 255 tgc cag atc gtc aac atc aaa ccg ggc cgg gtc ggc gga tac ctc gaa    816
Cys Gln Ile Val Asn Ile Lys Pro Gly Arg Val Gly Gly Tyr Leu Glu
            260                 265                 270 gcc cgc cgg gtg cac gac gtc tgc gcg gca cac ggg atc gcg gtg tgg    864
Ala Arg Arg Val His Asp Val Cys Ala Ala His Gly Ile Ala Val Trp
        275                 280                 285 tgc ggc ggg atg atc gag acc ggg ctc ggc cgg gcg gcc aac gtc gca    912
Cys Gly Gly Met Ile Glu Thr Gly Leu Gly Arg Ala Ala Asn Val Ala
    290                 295                 300 ctg gcc tcg ctg ccc ggc ttc acg ctg ccg ggg gac acc tcg gcg tcc    960
Leu Ala Ser Leu Pro Gly Phe Thr Leu Pro Gly Asp Thr Ser Ala Ser
305                 310                 315                 320 ggc cgg ttc tat cgc acc gac atc acc gag ccg ttc gtg ctg gac gcc   1008
Gly Arg Phe Tyr Arg Thr Asp Ile Thr Glu Pro Phe Val Leu Asp Ala
                325                 330                 335 ggg cat ctg ccg gtg ccg acc ggg ccg ggc ctc ggg gtg act ccg att   1056
Gly His Leu Pro Val Pro Thr Gly Pro Gly Leu Gly Val Thr Pro Ile
            340                 345                 350
```

```
ccg gat ctt ctg gac gag gtc acc acg gag aaa gcg tgg atc ggt tcg    1104
Pro Asp Leu Leu Asp Glu Val Thr Thr Glu Lys Ala Trp Ile Gly Ser
        355                 360                 365 tag                                                                 1107
```

<210> SEQ ID NO 2
<211> LENGTH: 368
<212> TYPE: PRT
<213> ORGANISM: Amycolatopsis orientalis

<400> SEQUENCE: 2

```
Val Lys Leu Ser Gly Val Glu Leu Arg Arg Val Arg Met Pro Leu Val
1               5                   10                  15

Ala Pro Phe Arg Thr Ser Phe Gly Thr Gln Ser Glu Arg Glu Leu Leu
            20                  25                  30

Leu Val Arg Ala Val Thr Pro Ala Gly Glu Gly Trp Gly Glu Cys Val
        35                  40                  45

Ala Met Glu Ala Pro Leu Tyr Ser Ser Glu Tyr Asn Asp Ala Ala Glu
    50                  55                  60

His Val Leu Arg Asn His Leu Ile Pro Ala Leu Leu Ala Ala Glu Asp
65                  70                  75                  80

Val Thr Ala His Lys Val Thr Pro Leu Leu Ala Lys Phe Lys Gly His
                85                  90                  95

Arg Met Ala Lys Gly Ala Leu Glu Met Ala Val Leu Asp Ala Glu Leu
            100                 105                 110

Arg Ala His Asp Arg Ser Phe Ala Ala Glu Leu Gly Ser Thr Arg Asp
        115                 120                 125

Ser Val Ala Cys Gly Val Ser Val Gly Ile Met Asp Ser Ile Pro His
    130                 135                 140

Leu Leu Asp Val Val Gly Gly Tyr Leu Asp Glu Gly Tyr Val Arg Ile
145                 150                 155                 160

Lys Leu Lys Ile Glu Pro Gly Trp Asp Val Glu Pro Val Arg Gln Val
                165                 170                 175

Arg Glu Arg Phe Gly Asp Asp Val Leu Leu Gln Val Asp Ala Asn Thr
            180                 185                 190

Ala Tyr Thr Leu Gly Asp Ala Pro Leu Leu Ser Arg Leu Asp Pro Phe
        195                 200                 205

Asp Leu Leu Leu Ile Glu Gln Pro Leu Glu Glu Asp Val Leu Gly
    210                 215                 220

His Ala Glu Leu Ala Lys Arg Ile Arg Thr Pro Ile Cys Leu Asp Glu
225                 230                 235                 240

Ser Ile Val Ser Ala Lys Ala Ala Asp Ala Ile Lys Leu Gly Ala
                245                 250                 255

Cys Gln Ile Val Asn Ile Lys Pro Gly Arg Val Gly Gly Tyr Leu Glu
            260                 265                 270

Ala Arg Arg Val His Asp Val Cys Ala Ala His Gly Ile Ala Val Trp
        275                 280                 285

Cys Gly Gly Met Ile Glu Thr Gly Leu Gly Arg Ala Ala Asn Val Ala
    290                 295                 300

Leu Ala Ser Leu Pro Gly Phe Thr Leu Pro Gly Asp Thr Ser Ala Ser
305                 310                 315                 320

Gly Arg Phe Tyr Arg Thr Asp Ile Thr Glu Pro Phe Val Leu Asp Ala
                325                 330                 335
```

```
                                      -continued

Gly His Leu Pro Val Pro Thr Gly Pro Gly Leu Gly Val Thr Pro Ile
            340             345             350

Pro Asp Leu Leu Asp Glu Val Thr Thr Glu Lys Ala Trp Ile Gly Ser
        355             360             365
```